United States Patent [19]

Helfenberger

[11] Patent Number: 4,795,640

[45] Date of Patent: Jan. 3, 1989

[54] OIL IN WATER EMULSION CONTAINING PROPETAMPHOS

[75] Inventor: Hans Helfenberger, Reinach, Switzerland

[73] Assignee: Sandoz Ltd., Basle, Switzerland

[21] Appl. No.: 58,967

[22] Filed: Jun. 8, 1987

[30] Foreign Application Priority Data

Jun. 16, 1986 [GB] United Kingdom ................ 8614647

[51] Int. Cl.$^4$ ............................................... A61K 9/10
[52] U.S. Cl. .................................... 424/405; 424/406; 424/407; 514/75; 514/76; 514/120; 514/137; 514/769; 514/770; 514/772; 514/783; 514/789; 514/875; 514/919; 514/920; 514/937; 514/938; 514/941; 514/943
[58] Field of Search ......... 424/405, 406, 407, DIG. 8, 424/DIG. 10; 514/75, 76, 137, 120, 770, 772, 783, 769, 789, 875, 919, 920, 937, 938, 941, 943; 558/182

[56] References Cited

U.S. PATENT DOCUMENTS

| | | | |
|---|---|---|---|
| 4,283,415 | 8/1981 | Fuyama et al. | 424/304 |
| 4,303,640 | 12/1981 | Fuyama et al. | 424/78 |
| 4,595,679 | 6/1986 | Broadbent | 514/67 |

FOREIGN PATENT DOCUMENTS

| | | |
|---|---|---|
| 0083437 | 7/1983 | European Pat. Off. . |
| 0111580 | 6/1984 | European Pat. Off. . |
| 0118759 | 9/1984 | European Pat. Off. . |
| 647132 | 1/1985 | Switzerland . |
| 2000972 | 1/1979 | United Kingdom . |
| 2088212 | 6/1982 | United Kingdom . |
| 2135886 | 9/1984 | United Kingdom . |
| 2176109 | 12/1986 | United Kingdom . |

OTHER PUBLICATIONS

K. Tsuji et al., "Development of Emulsion-Type Flowable Formulation", Proceedings of 5th International Congress of Pesticide Chemistry, Kyoto, Japan, 1982, vol. 2, 361-366.

T. Tadros, "Dispersion Science and Technology in Pesticidal Formulations", Proceeded 5th Int. Cong. Pesticidal Chemistry, Kyoto, Japan 1982, vol. 4, 245-253.

Primary Examiner—Morton Foelak
Assistant Examiner—Samuel A. Acquah
Attorney, Agent, or Firm—Gerald D. Sharkin; Richard E. Vila

[57] ABSTRACT

A solvent-free oil-in-water emulsion of propetamphos comprising
(a) 5 to 50% by weight of technical propetamphos in the form of droplets having a particle size of below 5 micron,
(b) 1 to 8% by weight of a polyvinyl alcohol,
(c) 1 to 3% by weight of a buffer, buffering the pH of the formulation to pH 6 to 7,
(d) 1 to 2% by weight of a vegetable oil,
(e) 0.5 to 2% by weight of an emulsifier
(f) 0 to 8% by weight of an antifreezing agent
(g) 0 to 0.1% by weight of an antifoaming agent (h) 0 to 0.1% by weight of a perfume, the balance being water, and a process of preparing such emulsion.

11 Claims, No Drawings

OIL IN WATER EMULSION CONTAINING PROPETAMPHOS

The present invention relates to solvent-free oil-in-water emulsions of propetamphos.

Propetamphos is the common name for a known insecticide, having the chemical name (E)-O-2-isopropoxycarbonyl-1-methylvinyl O-methyl ethylphosphoramidothioate.

Technical propetamphos is known to develop a strong unpleasant odour upon storage. Its shelf stability may be improved, e.g. with the aid of an acid scavenger or an aldehyde. If thus stabilised technical a.i. is incorporated in water-free, organic solvent-based formulations such as aerosols, emulsifiable concentrates (EC's), ready for use liquids etc., the development of bad odours may be inhibited during a shelf life of approx. 2 years. The term technical propetamphos as used hereinafter is intended to refer to technically prepared propetamphos having a purity of at least 86.0% by weight and comprising optionally up to 2.0% by weight of an acid scavenger or an aldehyde such as octanal.

Solvent-free oil-in-water emulsions (EW's) have many advantages over EC's. They are i.a. non-flammable, easier to handle, their transport and package can be done in plastic equipment, they are ecologically safer, less toxic and less irritant to mammals and less phytotoxic.

Technical propetamphos whether or not stabilised with an acid scavenger, or an aldehyde is however hydrolytically unstable; dissolved in water it has a half life of approx. 1 year at 25° C.

The objective of the present invention is to provide hydrostable EW's of propetamphos which do not develop bad odours during a shelf life of minimum 2 to 3 years. Further, the EW's should be easy to handle, have a viscosity allowing an easy pourability and allow an easy dilution to application forms in all kinds of water.

It has now been found that EW's of propetamphos comprising (a) 5 to 50% by weight of technical propetamphos in the form of droplets having a particle size of below 5 micron, (b) 1 to 8% by weight of a polyvinyl alcohol, (c) 1 to 3% by weight of a buffer, buffering the pH of the formulation to pH 6 to 7, (d) 1 to 2% by weight of a vegetable oil, (e) 0.5 to 2% by weight of an emulsifier (f) 0 to 8% by weight of an antifreezing agent (g) 0 to 0.1% by weight of an antifoaming agent (h) 0 to 0.1% by weight of a perfume, the balance being water, have the desired hydrostability and odour stability as well as other properties essential for an easy use and application of an EW.

Polyvinyl alcohols (PVA) suitable for use in the EW of the invention have conveniently a molecular weight of from 2000 to 125,000 and 11 to 28% of their hydroxy groups present in ester form, particularly in acetate ester form. Particularly suitable PVA's have a molecular weight of from 10,000 to 30,000 and a hydrolysation degree of 87 to 89 mole percent. The EW's of the invention will conveniently comprise from 4 to 8% by weight of PVA, but acceptable stability is also obtained with lower amounts of PVA.

It is believed that the main function of the PVA in the EW of the invention is that of a thickener and, in combination with a small amount of a suitable surfactant, that of a dispersing agent. To prevent sedimentation and phase separation, the density of the water phase should be raised as near as possible to the density of the oil phase (the density of propetamphos technical is approx. 1.13 g/ml at 20° C.). Conveniently the difference between the density of the aqueous phase and that of the oil phase of the emulsion should be smaller than 0.1 g/ml; very good results are obtained when the said difference in density is 0.05 g/ml or less, particularly when the difference is 0.02 g/ml or less.

It will be appreciated that the buffer system and any other ingredient present in the aqueous phase will also increase the density of said aqueous phase.

Essentially any buffer system allowing a pH stabilisation at pH 6 to 7 may be used, e.g. inorganic systems such as $KH_2PO_4$/NaOH and organic systems such as triethanolamine.HCl (preferably together with diNa ethylenediaminetetra acetic acid (diNa EDTA), trihydroxymethylaminoethane.HCl, imidazole.HCl etc., thereby taking into account the density requirements specified above.

The droplet size of the oil phase is conveniently smaller than 3 microns, preferably smaller than 2 micron, more preferably smaller than 1 micron. Such small droplets are obtained by means of conventional high shear stirring equipment (e.g. a Polytron® homogeniser, a Manton-Gaulin® homogeniser, an Ultraturrax® homogeniser) or with ultrasonic. Classical propeller stirrer, giving droplets of 2 micron or more, give coarser and less stable emulsions. One might have expected a decreased chemical stability with smaller droplets (the oil/water interface is larger with finer droplets). This is however not the case.

The vegetable oil has a surprisingly beneficial effect on the emulsion stability and prevents separation of serum. Examples of a suitable vegetable oil are soybean oil, peanut oil, cotton oil, sunflower oil and rape seed oil. The vegetable oil may be epoxidized; the degree of epoxidation is not essential.

Emulsifiers particularly suitable for use in the EW's of the invention are non-ionogenic (optionally in admixture with anionic emulsifiers) or zwitterionic. Their hydrophylic-lipophylic balance (HLB) is preferably between 13 and 14. Examples of such emulsifiers are ethoxylated castor oil, having 32 moles of ethylene oxide (commercially available from Sandoz Ltd. as Sandophor LM; HLB 14), ethoxylated oleylcetyl alcohol having 12 moles of ethylene oxide (commercially available from Sandoz Ltd. as Sandoxylate AOC-12; HLB 14), ethoxylated isooctylphenol having 10 moles of ethylene oxide (commercially available from Sandoz Ltd. as Sandoxylate® PO-10; HLB 14), PEG 600 monooleate (commercially available from Lankro as Nopco® 1125 B; HLB 13,5), PEG 1800 ricinoleate (commercially available from Lankro as Ethylan C 40 AH; HLB 13.5), a mixture of an ethoxylated triglyceride with Ca dodecylbenzene sulfonate (commercially available from ICI as Atlox® 4851 B; HLB 13,2) and cocoamidosulfobetaine (commercially available from Sandoz Ltd. as Sandobet® SC).

The viscosity of the EW conveniently does not exceed 300 mPa.s and is preferably below 250 mPa.s. Particularly preferred EW's have a viscosity of 50 to 150 mPa.s (each time measured with Rheomat 30 at 20° C. at a shear rate of 100 $s^{-1}$).

Where a good freeze-thaw stability of the EW's of the invention is required, the EW's will suitably comprise an antifreezing agent such as ethanol, propylene glycol, ethylene glycol, other glycols or mixtures thereof. A suitable amount of anti-freezing agent is in the range of from 4 to 8% by weight (of the EW).

To reduce foaming it may be desirable to add an anti-foaming agent, e.g. a silicone oil. In general 0.04 to 0.1% by weight will suffice to reduce foaming to an acceptable level.

Some minor amounts of perfume may also be added to give the EW the desired odour; amounts of from 0.01 to 0.1% by weight will in general suffice for that purpose.

The EW's of the invention are conveniently obtained by pouring, under vigorous stirring, an oil phase, comprising propetamphos, the vegetable oil and optionally a perfume, into an aqueous phase, comprising the PVA, the buffer system, the emulsifier and optionally an anti-foaming agent and/or an anti-freezing agent. The stirring is conveniently effected with a high shear agitation equipment, e.g. at 15-20,000 rpm. Equivalent ultrasonic equipments may be used as well. For treatment of, for example, a 500 g batch, high shear agitation for 1 to 20 minutes will in general suffice to obtain the desired droplet size.

The emulsion may become warm under these conditions and have to be cooled; it is coveniently cooled to room temperature after stirring.

For the preparation of the aqueous phase it is essential that the PVA is added to the water at room temperature, i.e. at 20° to 25° C., particularly at 23° C. The water/PVA mixture, which may also comprise the buffer system, the anti-foaming agent and the anti-freezing agent is then stirred for a short period of time at room temperature, to secure a good dispersion of the PVA in the water. The temperature of the mixture is then gradually increased to 50° C., while stirring, and stirring continued until a homogeneous mixture is obtained. The temperature of the mixture is then increased, up to a temperature of between 70° and 95° C., and said temperature maintained until all PVA is dissolved. The solution is then cooled to room temperature and the emulsifier stirred in.

The EW's of the invention offer advantages over EC's and other formulations with regard to safety (ecologically and in handling), phytotoxicity, packaging, corrosion of spray equipment etc. They are of particular interest for use in households, e.g. against cockroaches or ants (in spray form), or in dips (cattle dips or sheep dips).

In the following non-limitative Examples parts are by weight and temperatures in Centigrade.

EXAMPLES

| 1. Compositions (% w/w) | A | B | C | D |
|---|---|---|---|---|
| Propetamphos (tech.) | 22 | 51 | 21.1 | 51.1 |
| Polyvinylalcohol | 8 | 4 | 8.0 | 3.0 |
| Emulsifier | 1 | 1 | 1.0 | 1.0 |
| Vegetable oil | 1 | 1 | 1.0 | 1.0 |
| Perfume | 0.05 | 0.05 | — | — |
| $KH_2PO_4$ | 1.4 | 0.9 | 1.4 | 0.9 |
| NaOH (30%) | 0.87 | 0.55 | 0.87 | 0.55 |
| Propylene glycol | — | — | 8.0 | 4.0 |
| Antifoam | — | — | 0.1 | 0.04 |
| Water (demineralized) | 65.68 | 41.5 | 58.55 | 38.51 |
| | | | 100.0 | 100.0 |
| A.i. content (g/l at 20° C.) | | | 200 | 500 |

2. Raw Materials

The following is a specification of the raw materials used in Compositions A and B.

Propetamphos (technical), of 91% purity and containing 1.0% octanal.

Polyvinylalcohol: supplied by Kurashiki/CFS under the commercial name POVAL ® PVA-205, having a hydrolysation degree of 87 to 89%, a degree of polymerisation of 500 to 600, a (calculated) molecular weight of 22,000 to 26,000, a viscosity (at 4%, 20°; according to Höppler) of approx. 5 mPa.s and the appearance of a white, crystalline powder.

Emulsifier: a 50% solution in water of cocoamido sulfobetain, having a pH of 8±1 and the appearance of a clear, thin, yellow liquid.

Vegetable oil: epoxidised soybean oil, having 4.2 to 4.22 mVal/g epoxide groups (determined by $HClO_4$ titration), a viscosity (at 20°; according to Höppler) of 500 to 600 mPa.s and the appearance of a clear, yellowish liquid.

Perfume: supplied by Firmenich, Geneva, as perfume Citronvert 40.629, commercial name CIVER ®, having a flash point of ca. 60° and the appearance of a clear, yellow liquid.

The 30% NaOH solution had a density of 1.33+0.005.

3. Manufacture of Compositions A and B (Laboratory scale; emulsion batches of 500 g)

3.1 Oil Phase

Propetamphos, vegetable oil and perfume are mixed in a beaker by means of a magnetic stirrer.

The thus obtained oil phase has the following properties

| Oil phase of composition | A | B |
|---|---|---|
| appearance of solution | clear, yellow | clear, yellow |
| density | 1.117 g/ml | 1.120 g/ml |
| viscosity (Rheomat 30, $\eta_D$) | 57 mPa.s | 52 mPa.s |

3.2 Water Phase (in a sulfonation flask fitted with an anchor-stirrer and a reflux condenser)

$KH_2PO_4$ and 30% NaOH solution are dissolved in demineralized water. The polyvinylalcohol is then added within 2 minutes at 23°. After 15 minutes' stirring the mixture is warmed within 1 hour to 50°, stirred at that temperature for 1 hour and then heated at 75° until all polyvinylalcohol is dissolved (ca. 90 minutes). The solution is cooled to 25°, the emulsifier then stirred in and the whole mixture stirred for a further 15 minutes.

The thus obtained water phase has the following properties.

| Water phase of Composition | A | B |
|---|---|---|
| appearance of solution | clear, yellowish | clear, light yellow |
| density (g/ml) | 1.042 | 1.037 |
| viscosity (Rheomat 30, $\eta_D$) | 7.2 mPa.s | 7.1 mPa.s |

3.3 Emulsion

The water phase is stirred by means of a high shear stirrer at 15-20,000 rpm. and the oil phase poured into the water phase within 1½ to 2 minutes. The emulsion is further high shear stirred for 5 to 10 minutes (the temperature of the emulsion rises to 35° to 45°) and then cooled to room temperature.

The thus obtained emulsion compositions A and B remain liquid and unchanged down to −1°. For use/s- torage at lower temperatures the addition of an antifreezing agent is advantageous.

Both Compositions A and B remain completely stable (i.e. no sediment, no separation and serum and no development of bad odours is observed) for 8 weeks at 54° which is considered to correspond with a storage of 3 to 4 years at room temperature; they also have been found to remain readily dispersible after such heat treatment.

4. Manufacture of Compositions C and D

The compositions C and D are obtained as disclosed under point 3 for Compositions A and B, except as follows:

The oil phase is obtained by mixing propetamphos and vegetable oil in a beaker by means of a magnetic stirrer.

The water phase is obtained by dissolving $KH_2PO_4$ and the 30% NaOH solution in demineralized water followed by the addition of polyvinyl-alcohol and heating of the solution as disclosed under point 3.2, hereinabove. Said solution is cooled to 25°, emulsifier and propylene glycol stirred in, antifoam added and the mixture stirred to give the desired water phase.

The emulsifier employed is ethoxylated (32 mole) castor oil, commercial name Sandophor® LM (Sandoz Ltd.). The antifoam employed is a silicone oil, supplied by Rhône Poulenc, commercial name Rhodorsil® 426R.

The emulsion is then obtained by mixing the water phase and the oil phase as disclosed under point 3.3 above.

The thus obtained Compositions C and D are non-foaming and resist a 4 weeks' cyclo test (wherein the compositions are subject to alternate cooling for 6 hours to $-10°$ C. and heating for 6 hours to $+40°$ C.) without change in physical properties.

Similar results are obtained with formulations of the invention comprising technical propetamphos without an acid scavenger.

For combatting pests compositions of the invention are diluted with water to the desired protetamphos concentration and then applied to the pest locus in a pesticidally effective amount.

The compositions of the invention are particularly appropriate for use against public health pests (cockroaches, fleas). Said uses of propetamphos are known in the art. The concentrations of propetamphos to be applied are known in the art and are similar to those employed when applying propetamphos emulsifiable concentrates. Said concentration of propetamphos in application forms lies in general between 0.1 and 1% by weight, e.g. between 0.125 and 0.25% by weight for use against fleas and between 0.5 and 1.0% by weight for use against cockroaches.

I claim:

1. A solvent-free oil-in-water emulsion of propetamphos comprising
   (a) 5 to 50% by weight of technical propetamphos in the form of droplets having a particle size of below 5 micron,
   (b) 1 to 8% by weight of a polyvinyl alcohol,
   (c) 1 to 3% by weight of a buffer, buffering the pH of the formulation to pH 6 to 7,
   (d) 1 to 2% by weight of a vegetable oil,
   (e) 0.5 to 2% by weight of an emulsifier
   (f) 0 to 8% by weight of an antifreezing agent
   (g) 0 to 0.1% by weight of an antifoaming agent
   (h) 0 to 0.1% by weight of a perfume,
the balance being water.

2. The emulsion of claim 1, comprising from 4 to 8% by weight of polyvinyl alcohol.

3. The emulsion of claim 2, wherein the propetamphos droplets have a particle size of below 1 micron.

4. The emulsion of claim 3, wherein the polyvinyl alcohol has a molecular weight of from 2,000 to 125,000 and 11 to 28% of its hydroxy groups are present in acetate ester form.

5. The emulsion of claim 4, wherein the vegetable oil is selected from soybean oil, peanut oil, cotton oil, sunflower oil and rape seed oil, which oil may be epoxidized.

6. The emulsion of claim 5, wherein the vegetable oil is epoxidized soybean oil.

7. The emulsion of claim 6, wherein the buffer system is $KH_2PO_4$/NaOH.

8. The emulsion of claim 7, wherein the emulsifier is non-ionogenic, optionally in admixture with anionic emulsifiers, or zwitterionic and has a hydrophylic-lipophylic balance of between 13 and 14.

9. The emulsion of claim 8, wherein the antifreezing agent is a glycol and the antifoaming agent is a silicone oil.

10. The emulsion of claim 9, having a viscosity at 20° C. of from 50 to 150 mPa.s.

11. The emulsion of claim 10, wherein the difference between the density of its aqueous phase and that of its oily phase is smaller than 0.1 g/ml.

* * * * *